United States Patent
Ahmad et al.

(10) Patent No.: US 10,328,196 B2
(45) Date of Patent: Jun. 25, 2019

(54) SYSTEMS AND METHODS FOR PERIPHERAL VASCULAR CANNULATION

(71) Applicant: THE CLEVELAND CLINIC FOUNDATION, Cleveland, OH (US)

(72) Inventors: Usman Ahmad, Cleveland, OH (US); Michael Zhen-Yu Tong, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 0 days.

(21) Appl. No.: 15/725,349

(22) Filed: Oct. 5, 2017

(65) Prior Publication Data

US 2018/0104402 A1 Apr. 19, 2018

Related U.S. Application Data

(60) Provisional application No. 62/407,766, filed on Oct. 13, 2016.

(51) Int. Cl.
| | |
|---|---|
| *A61M 1/16* | (2006.01) |
| *A61M 1/36* | (2006.01) |
| *A61M 25/00* | (2006.01) |
| *A61M 39/10* | (2006.01) |

(52) U.S. Cl.
CPC ........ *A61M 1/3659* (2014.02); *A61M 1/1698* (2013.01); *A61M 1/3666* (2013.01); *A61M 25/0075* (2013.01); *A61M 39/10* (2013.01)

(58) Field of Classification Search
CPC .............. A61M 1/3689; A61M 1/1698; A61M 1/3666; A61M 39/10; A61M 25/007; A61M 2025/0079; A61M 2025/0031; A61M 2025/0018; A61M 25/0028; A61M 25/0029; A61M 25/003; A61M 25/0074

See application file for complete search history.

(56) References Cited

U.S. PATENT DOCUMENTS

| | | | |
|---|---|---|---|
| 4,643,712 A | 2/1987 | Kulik et al. | |
| 4,787,882 A | 11/1988 | Claren | |
| 5,626,564 A * | 5/1997 | Zhan | A61M 25/007 604/164.01 |
| 6,692,473 B2 | 2/2004 | St. Cyr et al. | |
| 7,695,452 B2 | 4/2010 | Lenker | |
| 8,992,455 B2 | 3/2015 | Segesser | |
| 9,168,352 B2 | 10/2015 | Kelly et al. | |
| 2007/0135791 A1* | 6/2007 | Slater | A61M 25/0029 604/508 |

(Continued)

FOREIGN PATENT DOCUMENTS

FR          2964877 A1      3/2012

OTHER PUBLICATIONS

Definition of Notch (Dictionary.com Mar. 27, 2018).*

(Continued)

*Primary Examiner* — Laura A Bouchelle
*Assistant Examiner* — Dung T Ulsh
(74) *Attorney, Agent, or Firm* — Tarolli, Sundheim, Covell & Tummino LLP

(57) ABSTRACT

Systems and method for peripheral cannulation are provided. Systems include cannulas defining fenestrations that can be exposed or occluded by a cover slip to selectively expose fenestrations to blood flow in an artery or vein.

20 Claims, 4 Drawing Sheets

(56) References Cited

U.S. PATENT DOCUMENTS

| | | | |
|---|---|---|---|
| 2013/0073015 A1* | 3/2013 | Rozenberg | A61F 7/0085 607/106 |
| 2014/0081134 A1* | 3/2014 | Fortson | A61M 25/003 600/435 |
| 2014/0163530 A1* | 6/2014 | Frenkel | A61M 25/003 604/540 |
| 2014/0276331 A1* | 9/2014 | Bian | A61M 1/3659 604/8 |
| 2014/0276602 A1* | 9/2014 | Bonnette | A61M 25/007 604/508 |
| 2015/0316404 A1* | 11/2015 | Krivitski | G01F 22/02 702/19 |
| 2017/0056622 A1* | 3/2017 | O'Flynn | A61M 25/0017 |
| 2017/0106167 A1* | 4/2017 | Hobbs | A61M 25/0074 |
| 2017/0112979 A1* | 4/2017 | Masuda | A61M 1/0064 |
| 2017/0325713 A1* | 11/2017 | Burkholz | A61B 5/062 |
| 2017/0368306 A1* | 12/2017 | Tal | A61B 17/12186 |
| 2018/0001012 A1* | 1/2018 | Ardehali | A61M 1/1698 |
| 2018/0043119 A1* | 2/2018 | Bateman | A61M 16/0468 |
| 2018/0049747 A1* | 2/2018 | Tal | A61B 17/12186 |

OTHER PUBLICATIONS

Definition of Tube (Dictionary.com Mar. 27, 2018).*
Search Report for corresponding application No. PCT/US2017/055228, dated Dec. 19, 2017, pp. 1-13.

* cited by examiner

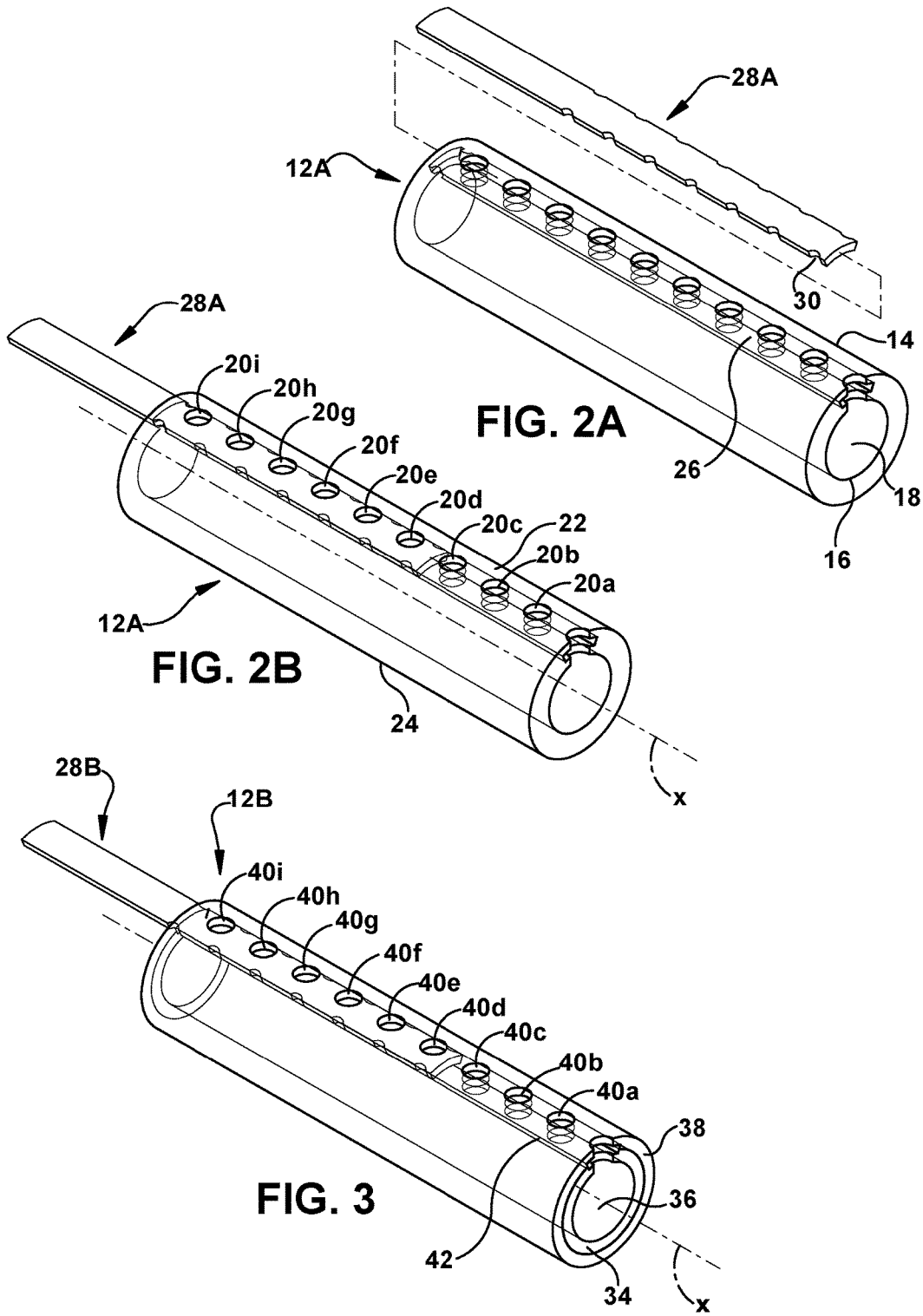

US 10,328,196 B2

SYSTEMS AND METHODS FOR PERIPHERAL VASCULAR CANNULATION

CROSS-REFERENCE TO RELATED APPLICATIONS

The present application claims priority to U.S. Provisional Application No. 62/407,766, filed on Oct. 13, 2016, the entirety of which is incorporated by reference herein.

TECHNICAL FIELD

The present invention relates to systems and methods for peripheral arterial and venous cannulation.

BACKGROUND

Percutaneous arterial and venous cannulation is used in a wide variety of medical procedures. For example, peripheral arterial and venous cannulation is often required for short, intermediate and long term circulatory support in patients with cardiopulmonary compromise. Extracorporeal Membrane Oxygenation (ECMO) is a form of partial cardiopulmonary bypass used for long-term support of respiratory and/or cardiac function. ECMO is primarily indicated for patients with such severe ventilation and/or oxygenation problems that they are unlikely to survive conventional mechanical ventilation. ECMO often involves shunting blood around the heart and lungs through an extracorporeal blood circuit and membrane oxygenator. Roller or centrifugal heart-lung bypass pumps are used to circulate blood through the ECMO circuit. Treatment courses can be as short as a few days or as long as a month or more.

There are different forms of ECMO such as venoarterial (VA), venovenous (VV) and arterio-venous (AV). VA ECMO takes deoxygenated blood from a central vein or the right atrium, pumps it past the oxygenator, and then returns the oxygenated blood, under pressure, to the arterial side of the circulation (typically to the aorta). This form of ECMO partially supports the cardiac output as the flow through the ECMO circuit is in addition to the normal cardiac output. Typically, patients with cardiac insufficiency require VA-ECMO. In the case of VA ECMO, an approximately 20F (6-7 mm internal diameter) arterial cannula is placed in the femoral artery, for example, but such arteries are typically much smaller, particularly in children or other smaller patients.

VV-ECMO takes blood from a large vein and returns oxygenated blood back to a large vein. Typically patient with respiratory insufficiency not amendable to ventilator support require VV-ECMO. In VV ECMO, either two large cannulas are placed in two separate extremity veins or a single dual lumen cannula is placed in one extremity. These cannulas remove blood from central circulation and return oxygenated blood to the right atrium. Often a 31F (10 mm internal diameter) cannula is placed in the internal jugular vein or the subclavian vein.

Due to the large size of the cannulas used in ECMO, the venous drainage in the extremity or head and neck region where a cannula is placed is significantly impaired. Many patients develop venous stasis, thrombosis, and edema in the extremity. Intracranial venous hypertension has been well described in the case of internal jugular vein cannulation, especially in children. On the arterial side, if a femoral artery is cannulated, the blood is often returned into the abdominal aorta and there is no perfusion to the leg on the side of cannulation. This can lead to drastic ischemic complications.

Presently, if arterial cannulation is required for more than a few hours, a second smaller cannula is placed in the femoral artery for antegrade perfusion.

Accordingly, a need exists for a cannula that provides adequate proximal venous drainage and distal arterial perfusion during peripheral cannulation procedures.

BRIEF DESCRIPTION OF THE DRAWINGS

FIG. 2A is an exploded view of a cannula with a coverslip inserted into a channel thereof according to an embodiment of the present disclosure.

FIG. 2B is a perspective view of the cannula of FIG. 2A with the coverslip of FIG. 2B inserted into a channel of the cannula.

FIG. 3 is a perspective view of a cannula with a cover slip inserted into a channel thereof according to another embodiment of the present disclosure.

SUMMARY

Figure 1:
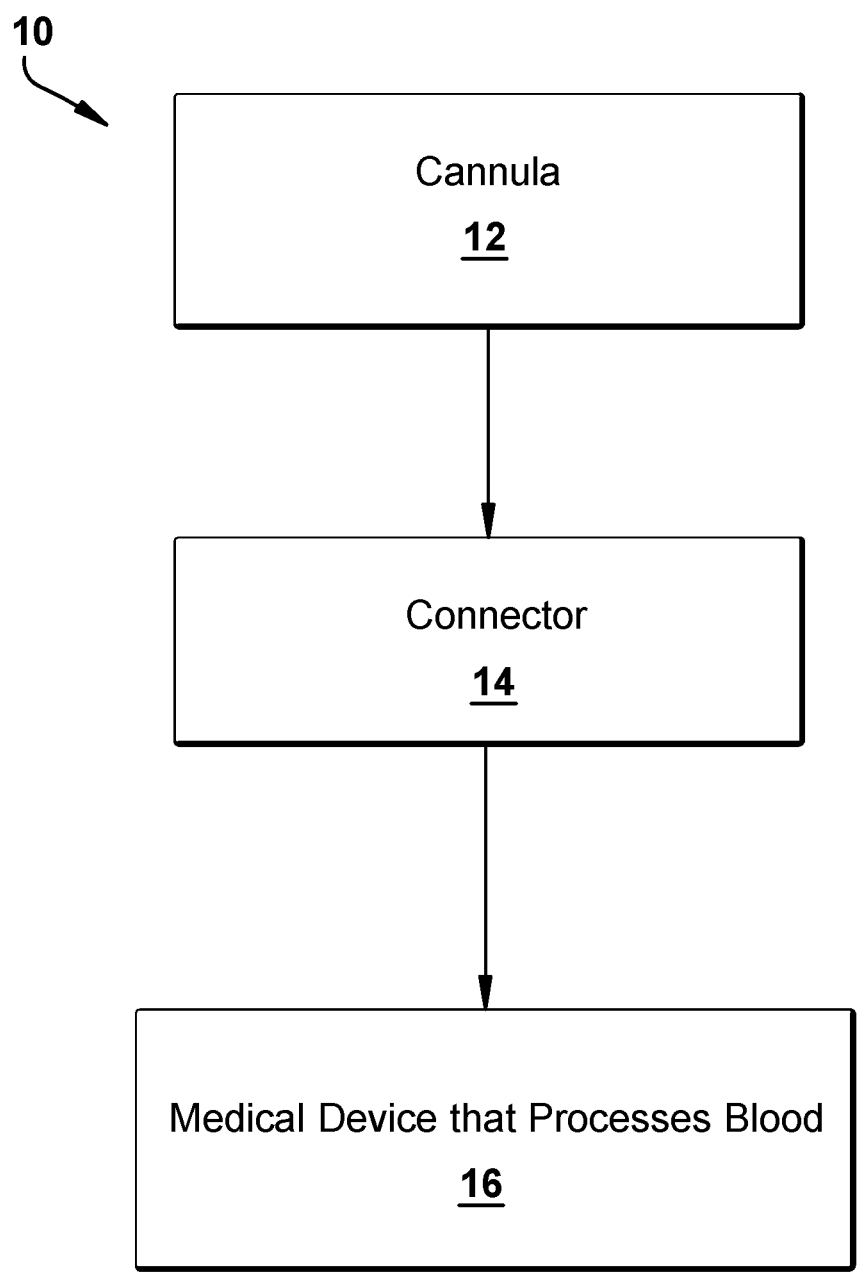
FIG. 1 is flow chart depicting components of a system according to an embodiment of the present disclosure.

The present disclosure relates to systems and methods of vascular cannulation. A system can include a cannula, a cover slip, a medical device, and a connector. In an embodiment, a system comprises a cannula that has a longitudinal axis and comprises an outer wall and an inner wall that defines a lumen. Fenestrations are located along the longitudinal axis, extend through the outer and inner wall, and are in fluid communication with the lumen. The cannula also includes a channel that extends along the longitudinal axis between the inner and outer walls and that is aligned with the fenestrations. The system further includes a cover slip that is slidable within the channel and sized and shaped to occlude the fenestrations. The system also includes a medical device that processes blood and a connector sized and shaped to connect the medical device to the cannula.

In another embodiment, a system comprises a cannula having a longitudinal axis. The cannula includes an outer tube and an inner tube defining a lumen. Fenestrations are located along the longitudinal axis, extend through the outer and inner tubes, and are in fluid communication with the lumen. A channel extends along the longitudinal axis between the outer and inner tubes and is aligned with the fenestrations. The system further includes a cover slip that is slidable within the channel and is sized and shaped to occlude the fenestrations. The system also includes a medical device that processes blood and a connector sized and shaped to connect the medical device to the cannula.

In another embodiment, a method that can be used in a cannulation procedure is provided. The method comprises obtaining a cannula having a longitudinal axis and a first and second portion. The cannula comprises an outer wall and an inner wall that defines a lumen. The cannula also includes fenestrations that are located along the longitudinal axis, extend through the outer and inner wall, and are in fluid communication with the lumen. The cannula further includes a channel extending along the longitudinal axis between the inner and outer wall and aligned with the fenestrations. The method further includes inserting the first portion of the cannula inside a peripheral artery or vein. The method also includes sliding a cover slip into the channel. The covers slip is sized and shaped to occlude the fenestrations. The method further includes retrieving proximally the cover slip to a position such that the fenestrations of the first portion of the cannula are exposed to the peripheral artery or vein while the fenestrations of the second portion are occluded. The method includes connecting the cannula to a medical device that processes blood.

DETAILED DESCRIPTION

As used herein with respect to a described element, the terms "a," "an," and "the" include at least one or more of the described element unless otherwise indicated. Further, the term "or" and "and" refer to "and/or" unless otherwise indicated. In addition, it will be understood that when an element is referred to as being "over," "on," "attached" to, "connected" to, "coupled" with, "contacting," "in fluid communication with," etc., another element, it can be directly over, on, attached to, connected to, coupled with, contacting, or in fluid communication with the other element or intervening elements may also be present. In contrast, when an element is referred to as being "directly over," "directly on," "directly attached" to, "directly connected" to, "directly coupled" with, "directly contacting," or in "direct fluid communication" with another element, there are no intervening elements present. It will also be appreciated that references to an element that is disposed "adjacent" another element may have portions that overlap or underlie the adjacent element. As used herein, a "patient" is mammal such as, for example, a human being.

The present disclosure relates to systems and methods of vascular cannulation, such as peripheral vascular cannulation. Referring to FIG. 1, in certain aspects, system 10 is provided that includes cannula 12, medical device that processes blood 16, and connector 14 that is sized and shaped to attach cannula 12 to medical device 16.

Referring to FIGS. 2A and 2B, in an embodiment, cannula 12A comprises outer wall 14 and inner wall 16 that defines lumen 18. Fenestrations 20 are located along longitudinal axis X, extend through outer wall 14 and inner wall 16, and are in fluid communication with lumen 18. The fenestrations can extend along the entire length of the cannula or a portion less than the entire length. In certain aspects, cannula 12 has first side 22 and opposing second side 24. First side 22 defines fenestrations 20 and fenestrations 20 do not extend through second side 24 of cannula 12. Cannula 12 further includes channel 26 that extends along longitudinal axis X between outer wall 14 and inner wall 16 and that is aligned with fenestrations 20. In another embodiment, the cannula has an inner tube and a concentric outer tube. For example, referring to FIG. 3, cannula 12B has an inner tube 34 defining lumen 36 and outer tube 38 disposed about inner tube 32. Fenestrations 40 are located along longitudinal axis X and are in fluid communication with lumen 36. Cannula 12B further includes channel 42 that extends along longitudinal axis X between outer tube 38 and inner tube 34 and that is aligned with fenestrations 40.

In either embodiment, the system further a cover slip 28 slidable within channel 26 of cannula 12 (cover slip 28A) or channel 42 of cannula 12B (coverslip 28B) and sized and shaped to occlude fenestrations 20 and 40 of cannulas 12A and 12B respectively. In certain embodiments, the cover slip can have an inner lumen that can receives tubing or other devices that may be used in the medical procedure for which the cannula is used. The cover slip can also include guides to ensure the cover slip is in the proper position in the channel of the cannula. For example, as shown in FIGS. 2A and 2B, cover slip 28A can include guides at a portion thereof, such as distal portion to ensure cover slip 28A is in the correct position in relation to the other components of the cannula such as the fenestrations of the cannula. FIG. 2 illustrates cover slip 28A having detent notches 30 but other types of guides can be used that ensure the cover slip is in the correct position. A cover slip can also include fenestrations that are aligned with the fenestrations of the inner wall or inner tube.

System 10 also includes medical device that processes blood 16. A medical device that processes blood is a medical device that stores, analyzes, samples, collects, pumps, inflows, outflows, or transmits therapeutic agents to blood of a patient. Non-limiting examples of medical devices that process blood include hemodynamic monitoring devices and extracorporeal support (ECS) circuits. ECS circuits include ECMO circuits such as VV-ECMO, VA-ECMO and AV-ECMO circuits. The ECS circuit can also be a cardiopulmonary bypass machine.

System 10 further includes connector 14 sized and shaped to connect medical device 16 to cannula 12. Non-limiting examples of connectors include luer-type fittings, clamps, adhesives, clips, or various types of male-female fasteners.

Figure 4:
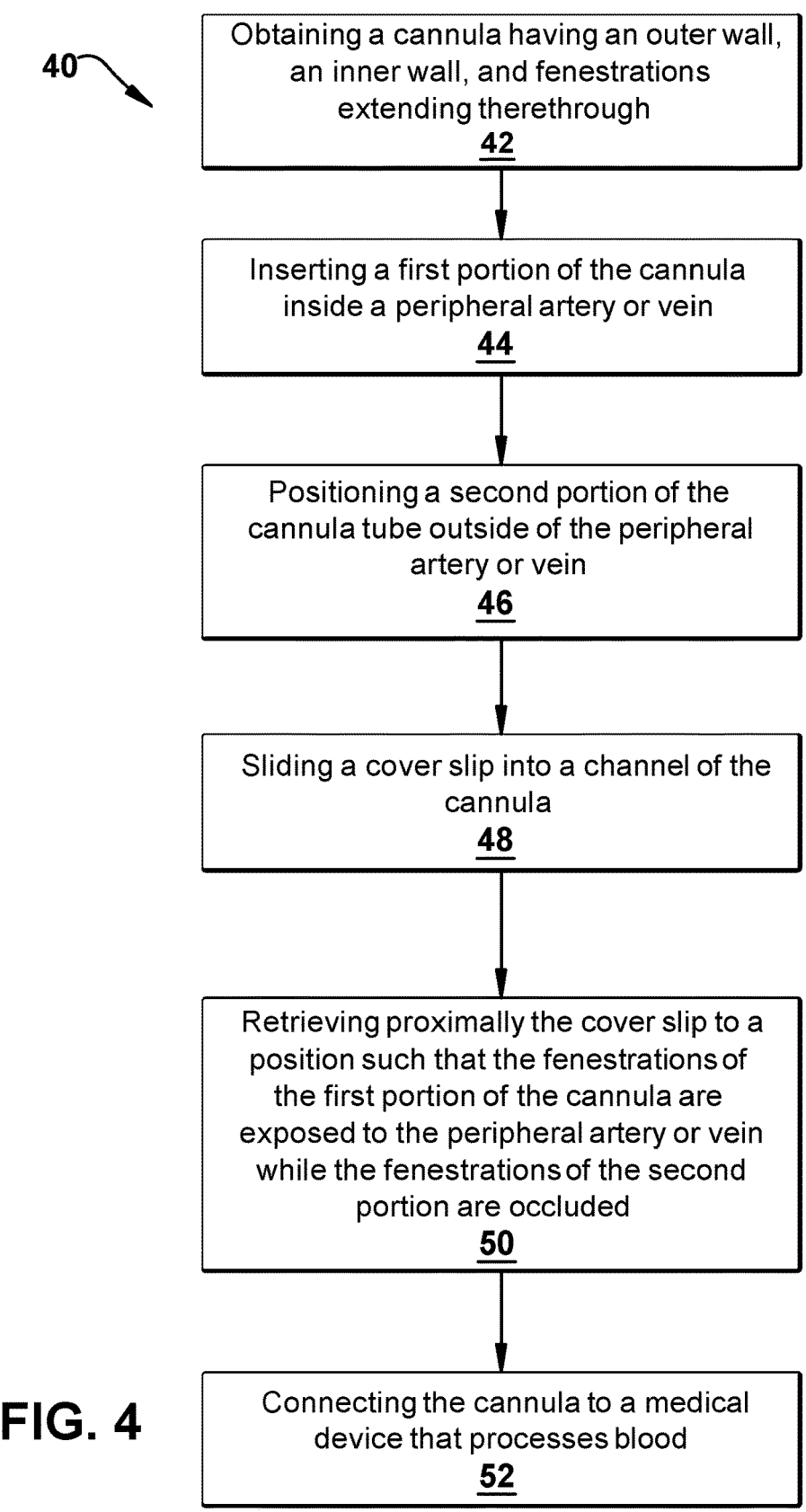
FIG. 4 is a flow chart depicting steps of a method of using an embodiment of a system of the present disclosure in a cannulation procedure.

Certain aspects of the present disclosure provide a method that can be used during a peripheral cannulation procedure such as, for example, an ECMO or cardiopulmonary bypass procedure. Referring to FIG. 4, method 40 includes obtaining a cannula, as described above, having a first portion and a second portion (step 42). For example, in an embodiment, the cannula has an outer wall and an inner wall that defines a lumen. Fenestrations extend along the length of the cannula. The fenestrations are in fluid communication with the lumen of the inner wall. The cannula has a channel that extends along the longitudinal axis between the inner and outer wall and that is aligned with the fenestrations of the cannula. The method further includes inserting the first portion of the cannula inside a peripheral artery or vein (step 44) and positioning the second portion of the cannula outside of the peripheral artery or vein (step 46). The method includes sliding a cover slip into the channel of the cannula (step 48). The cover slip is sized and shaped to occlude the fenestrations of the cannula. The method also includes retrieving proximally the cover slip to a position such that the fenestrations of the first portion of the cannula are exposed to the peripheral artery or vein while the fenestrations of the second portion are occluded (step 50). The method also includes connecting the cannula to a medical device that processes blood (step 52).

Figure 5A:
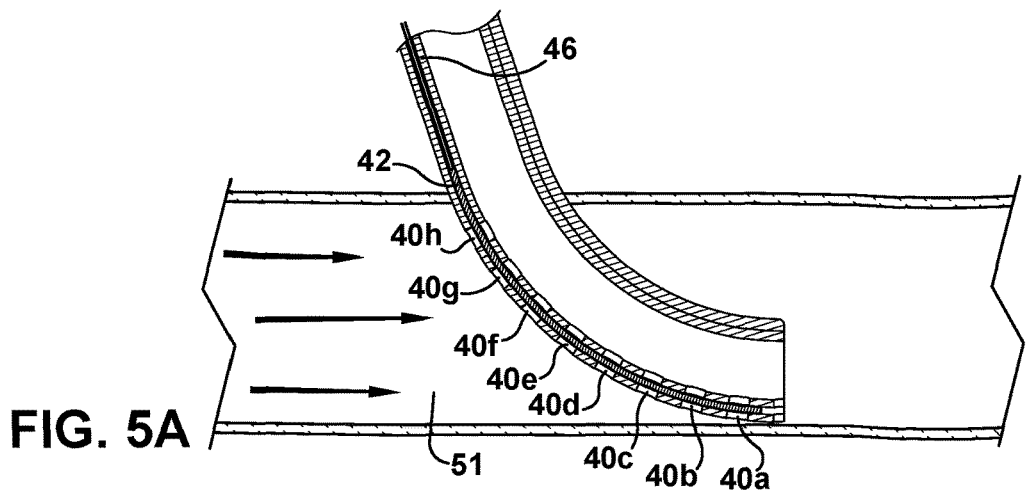
FIG. 5A-5C is a schematic illustration of a cover slip being retrieved proximally from a blood vessel to expose the blood vessel to fenestrations of an inner wall of a cannula according to an embodiment of the present disclosure.
Figure 5B:
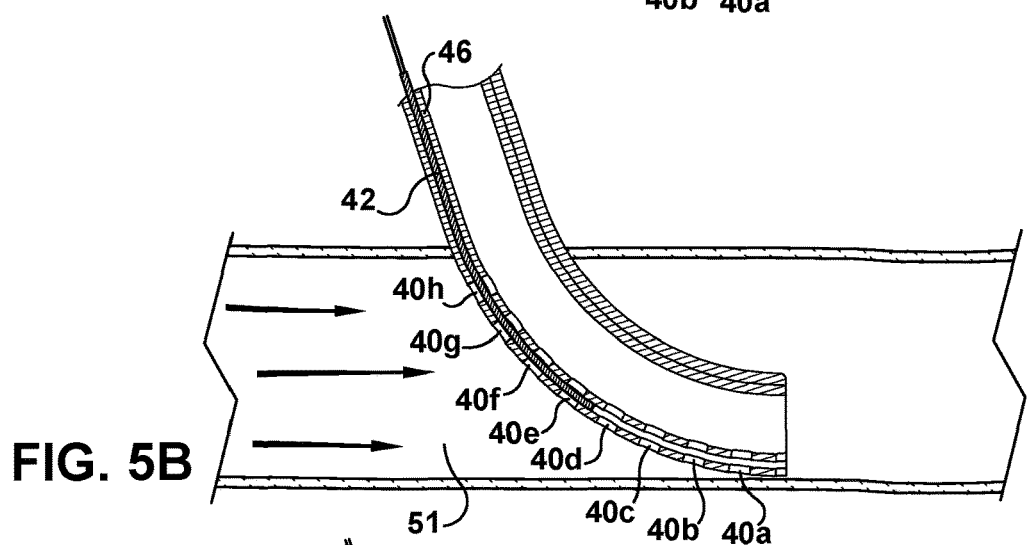
Figure 5C:
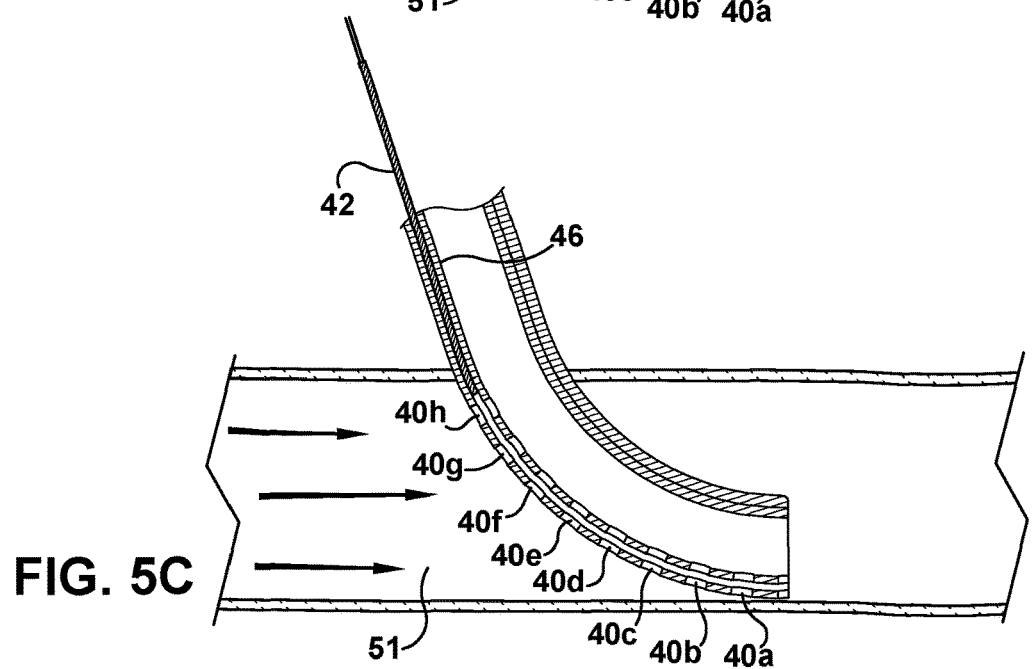

As schematically shown in FIG. 5A-5C, in use, cover slip 42 can be retrieved proximally to expose any number of fenestrations 44 of cannula 46 to the artery or vein 51. Since the depth of cannula insertion is different for every patient, the operator can retrieve the cover slip back to the level of insertion into the vessel such that the fenestrations inside the vessel are open while those outside the vessel remain occluded. In embodiments where one side of the inner tube defines the fenestrations, the cover slip can be retrieved back to open any number of fenestrations to the blood vessel lumen towards the side that is being blocked by the cannula itself. In the case of peripheral venous cannulation, features of a cannula as described herein allow drainage of venous blood from the extremity into the cannula and thus into the medical device, such as an ECS circuit. In the case of peripheral arterial cannulation, such features allow perfusion of the artery and extremity distal to the cannulation site as indicated by the arrows.

Cannulas and methods as disclosed herein can eliminate steps in certain cannulation procedures. For example, if a femoral artery is cannulated and the cannula needs to remain in the artery for more than a couple of hours, a second smaller cannula is placed for antegrade perfusion to prevent ischemic complications. With cannulas as disclosed herein, only one cannula is necessary in the femoral artery as the cover slip and fenestrations allow access to the vessel lumen on the side being blocked by the cannula. Such cannulas can be smaller than those currently used to achieve the same degree of drainage, decreasing vascular complication rates as well as preventing ischemia without inserting a second reperfusion cannula. Further, the fenestrations of cannulas as disclosed herein provide flexibility regarding the distance the cannula is inserted in the blood vessel. Cannulas as described herein address the problem of inadequate venous drainage at the site of venous cannulation and inadequate antegrade perfusion at the site of arterial cannulation. Such cannulas can prevent stasis, venous thrombosis, improves blood flow and prevent ischemia (without necessarily inserting a second reperfusion cannula). Cannulas as described herein also can be used for longer term and can be smaller than current cannulas to achieve the same degree of drawing, which can decrease vascular complication rates.

Cannulas as disclosed herein can be used for several different indications. As mentioned above, cannulas can be used for ECMO, cardiopulmonary bypass procedures and other cardiovascular perfusion procedures. Cannulas as disclosed herein can also be used during organ transplant procedures, such as lung transplant procedures. Cannulas can be used for the adult population as well as the pediatric population. Depending on the indication and patient, the cannulas can be implanted for different periods of times and have different sizes. For example, if implanted into the neck, a cannula can be about 50 centimeters (cm). If implanted in the groin, the cannula can be about 100 cm. If used for ECMO, a cannula can be implanted for up to 100 days and for cardiopulmonary bypass cannulation approximately 3 to 4 hours. In terms of sizes, for pediatric procedures, the cannula can have a size of approximately 8 Fr. Such indications and sizes are exemplary and cannulas as disclosed herein can be used for other suitable indications and have other configurations.

Each of the disclosed aspects and embodiments of the present disclosure may be considered individually or in combination with other aspects, embodiments, and variations of the present disclosure. Further, while certain features of embodiments of the present disclosure may be shown in only certain figures, such features can be incorporated into other embodiments shown in other figures while remaining within the scope of the present disclosure. In addition, unless otherwise specified, none of the steps of the methods of the present disclosure are confined to any particular order of performance.

What is claimed is:

1. A system comprising:
   a cannula having a longitudinal axis and comprising:
      an outer wall;
      an inner wall defining a lumen;
      a plurality of fenestrations located and spaced apart from each other along the longitudinal axis, each of the plurality of fenestrations having one end extending through the outer wall and an opposing end extending through the inner wall, and in fluid communication with the lumen defined by the inner wall, the inner wall and the outer wall longitudinally fixed relative to each other; and
      a channel extending along the longitudinal axis between the outer and inner walls and aligned with the plurality of fenestrations;
   a cover slip slidable within the channel and sized and shaped to occlude each of the plurality of fenestrations;
   a medical device that processes blood; and
   a connector sized and shaped to connect the medical device to the cannula.

2. The system of claim 1, wherein the cannula has a first side and an opposing second side, the first side defining the plurality of fenestrations, the plurality of fenestrations not extending through the second side of the cannula.

3. The system of claim 1, wherein the cover slip comprises a guide at a portion thereof.

4. The system of claim 3, wherein the guide is a dented notch.

5. The system of claim 1, wherein the medical device is a hemodynamic monitoring device.

6. The system of claim 1, wherein the medical device is an extracorporeal support (ECS) circuit.

7. The system of claim 6, wherein the ECS circuit is an extracorporeal membrane oxygenatio (ECMO) circuit.

8. The system of claim 7, wherein the ECMO circuit is a veno-venous ECMO (VV-ECMO) circuit, a veno-arterial ECMO (VA-ECMO) or an arterio-venous (AV-ECMO) circuit.

9. The system of claim 6, wherein the ECS circuit is a cardiopulmonary bypass machine.

10. A system comprising:
    a cannula having a longitudinal axis and comprising:
       an outer tube;
       an inner tube defining a lumen;
       a plurality of fenestrations located and spaced apart from each other along the longitudinal axis, each of the plurality of fenestrations having one end extending through the outer tube and another end extending through the inner tube and in fluid communication with the lumen defined by the inner tube, the inner tube and the outer tube longitudinally fixed relative to each other; and
       a channel extending along the longitudinal axis between the outer and inner tubes and aligned with the plurality of fenestrations;
    a cover slip slidable within the channel and sized and shaped to occlude each of the plurality of the fenestrations;
    a medical device that processes blood; and
    a connector size and shaped to connect the medical device to the cannula.

11. The system of claim 10, wherein the cannula has a first side and an opposing second side, the first side defining the plurality of fenestrations, the plurality of fenestrations not extending through the second side of the cannula.

12. The system of claim 10, wherein the medical device is a hemodynamic monitoring device.

13. The system of claim 10, wherein the medical device is an extracorporeal support (ECS) circuit.

14. The system of claim 13, wherein the ECS circuit is a cardiopulmonary bypass machine.

15. A method comprising:
    obtaining a cannula having a longitudinal axis and a first and second portion, the cannula comprising:
       an outer wall;
       an inner wall defining a lumen;

a plurality of fenestrations located and spaced apart from each other along the longitudinal axis, each of the plurality of fenestrations having one end extending through the outer wall and an opposing end extending through the inner wall, and in fluid communication with the lumen, the inner wall and the outer wall longitudinally fixed relative to each other; and a channel extending along the longitudinal axis between the outer and inner wall and aligned with the plurality of fenestrations;

inserting the first portion of the cannula inside a peripheral artery or vein;

positioning the second portion of the cannula outside of the peripheral artery or vein;

sliding a cover slip into the channel, the cover slip sized and shaped to occlude the plurality of fenestrations;

retrieving proximally the cover slip to a position such that the plurality fenestrations of the first portion of the cannula are exposed to the peripheral artery or vein while the plurality of fenestrations of the second portion are occluded; and connecting the cannula to a medical device that processes blood.

16. The method of claim 15, wherein positioning the second portion of the cannula outside of the peripheral artery or vein is positioning the second portion at the level of insertion into the peripheral artery or vein.

17. The method of claim 15, wherein the medical device is a hemodynamic monitoring device.

18. The method of claim 15, wherein the medical device is an ECS circuit.

19. The method of claim 18, wherein the ECS circuit is an ECMO circuit.

20. The method of claim 18, wherein the ECS circuit is a cardiopulmonary bypass machine.

* * * * *